United States Patent
Malm et al.

(10) Patent No.: US 7,319,096 B2
(45) Date of Patent: *Jan. 15, 2008

(54) THYROID HORMONE RECEPTOR ANTAGONISTS FOR CARDIAC AND METABOLIC DISORDERS II

(75) Inventors: Johan Malm, Skogas (SE); Peter Brandt, Solna (SE); Karin Edvinsson, Stockholm (SE); Thomas Ericsson, Enhorna (SE); Sandra Gordon, Mariefred (SE)

(73) Assignee: Karo Bio AB, Huddinge (SE)

( * ) Notice: Subject to any disclaimer, the term of this patent is extended or adjusted under 35 U.S.C. 154(b) by 234 days.

This patent is subject to a terminal disclaimer.

(21) Appl. No.: 10/477,676

(22) PCT Filed: Apr. 15, 2002

(86) PCT No.: PCT/EP02/04193

§ 371 (c)(1),
(2), (4) Date: Jun. 10, 2004

(87) PCT Pub. No.: WO02/092550

PCT Pub. Date: Nov. 21, 2002

(65) Prior Publication Data

US 2004/0220147 A1     Nov. 4, 2004

(30) Foreign Application Priority Data

May 15, 2001   (GB)   .................................. 0111861.1

(51) Int. Cl.
| | |
|---|---|
| A61K 31/426 | (2006.01) |
| A61K 31/42 | (2006.01) |
| A61K 64/192 | (2006.01) |
| A61K 31/165 | (2006.01) |
| C07D 277/22 | (2006.01) |
| C07D 263/32 | (2006.01) |
| C07C 309/19 | (2006.01) |
| C07C 259/06 | (2006.01) |

(52) U.S. Cl. .................. 514/79; 514/366; 514/374; 514/576; 514/617; 548/203; 548/247; 562/108; 562/465; 562/621

(58) Field of Classification Search ................ 562/465, 562/472, 108, 621; 514/79, 366, 374, 576, 514/617; 548/203, 247
See application file for complete search history.

(56) References Cited

FOREIGN PATENT DOCUMENTS

| WO | 99/00353 | 1/1999 |
|---|---|---|
| WO | 00/07972 | 2/2000 |
| WO | 01/36365 | 5/2001 |

OTHER PUBLICATIONS

Silverman, Richard, The Organic Chemistry of Drug Design and Drug Action, 1992, Academic Press, Inc, p. 19-23.*
Gonzalez-Sancho et al, Thyroid hormone receptors/THR gene in human cancer, 2003, 192, Cancer Letters, p. 121-132.*
Forrest, Douglas, The Thyroid Hormone Receptor Family: Insights from Knockouts, Sep. 2002, 3, Hot Thyroidology, p. 1-4.*
Chiellini, G. et al. "A High-Affinity Subtype-Selective Agonist for the Thyroid Hormone Receptor," *Chemistry and Biology*, vol. 5, No. 6, pp. 299-306 (1998).
L. M. Lima and E. J. Barreio, "*Bioisosterism: A Useful Strategy for Molecular Modification and Drug Design*", Current Medical Chemistry, vol. 12, No. 1, pp. 23-49 (2005).
George A. Patani and Edmond J. Lavoie, "*Bioisosterism: A Rational Approach in Drug Design*," Chemical Reviews, vol. 96, No. 8, pp. 3147-3176 (Jul. 25, 1996).

* cited by examiner

*Primary Examiner*—Kamal A. Saeed
*Assistant Examiner*—Karen Cheng
(74) *Attorney, Agent, or Firm*—Wiggin and Dana LLP; Todd E. Garabedian; Elizabeth A. Galletta

(57) ABSTRACT

This invention relates to novel compounds which are thyroid receptor ligands, preferably antagonists, and to methods for using such compounds in the treatment of cardiac and metabolic disorders, such as cardiac arrhythmias, thyrotoxicosis, subclinical hyperthyrodism and liver diseases.

11 Claims, No Drawings

THYROID HORMONE RECEPTOR ANTAGONISTS FOR CARDIAC AND METABOLIC DISORDERS II

CROSS-REFERENCE TO RELATED APPLICATIONS

This application is a US National Stage application of International Patent Application No. PCT/EP02/04193 filed 15 Apr. 2002.

FIELD OF THE INVENTION

This invention relates to novel compounds which are thyroid receptor ligands, preferably antagonists, and to methods for using such compounds in the treatment of cardiac and metabolic disorders, such as cardiac arrhythmias, thyrotoxicosis, subclinical hyperthyrodism and liver diseases.

BACKGROUND OF THE INVENTION

Nuclear hormone receptors comprise a class of intracellular mostly ligand-regulated transcription factors, which include receptors for thyroid hormones. Thyroid hormones exert profound effects on growth, development and homeostasis in mammals. They regulate important genes in intestinal, skeletal and cardiac muscles, liver and the central nervous system, and influence the overall metabolic rate, cholesterol and triglyceride levels, heart rate, and affect mood and overall sense of well being.

There are two major subtypes of the thyroid hormone receptor, TRα and TRβ, expressed from two different genes. Differential RNA processing results in the formation of at least two isoforms from each gene. The $TR\alpha_1$, $TR\beta_1$ and $TR\beta_2$ isoforms bind thyroid hormone and act as ligand-regulated transcription factors. The $TR\alpha_2$ isoform is prevalent in the pituitary and other parts of the central nervous system, does not bind thyroid hormones, and acts in many contexts as a transcriptional repressor. In adults, the $TR\beta_1$ isoform is the most prevalent form in most tissues, especially in the liver and muscle. The $TR\alpha_1$ isoform is also widely distributed, although its levels are generally lower than those of the $TR\beta_1$ isoform. A growing body of data suggest that many or most effects of thyroid hormones on the heart, and in particular on the heart rate and rhythm, are mediated through the $TR\alpha_1$ isoform, whereas most actions of the hormones on the liver, muscle and other tissues are mediated more through the β-forms of the receptor. It is believed that the α-isoform of the receptor is the major drive to heart rate for the following reasons: (i) tachycardia is very common in the syndrome of generalized resistance to thyroid hormone in which there are defective TRβ-isoforms, and consequently high circulating levels of $T_4$ and $T_3$; (ii) Tachycardia was observed in the only described patient with a double deletion of the TRβ gene (Takeda et al, *J. Clin. Endrocrinol. & Metab.* 1992, 74, 49); (iii) a double knockout TRα gene (but not β-gene) in mice showed bradycardia and lengthening of action potential compared to control mice (Functions of Thyroid Hormone Receptors in Mice: D. Forrest and B. Vennström, Thyroid, 2000, 10, 41-52); (iv) western blot analysis of human myocardial TRs show presence of the $TR\alpha_1$, $TR\alpha_2$ and $TR\beta_2$ proteins, but not $TR\beta_1$.

If the indications above are correct, an α-selective thyroid hormone receptor antagonist that interacts selectively with the heart would offer an attractive alternative treatment of heart related disorders, such as atrial and ventricular arrhythmias.

Atrial fibrillation (AF) is the most common type of sustained arrhythmia encountered in primary care practice and is significantly more common in elderly patients, thus reflecting a reduction in the threshold for AF with age. Pharmacological treatment of AF involves the following types of anti-arrhythmic drugs according to Vaughan-Williams classification: (i) of class I such as disopyramide and flecainide (sodium channel blocker); (ii) of class III such as amiodarone (potassium channel blocker, prolongation of repolarization); (iii) of class IV such as verapamil and dilitazem (calcium channel blocker). Many patients are also subjected to electric cardioversions in order to convert atrial fibrillation into sinus rhythm. It should be noted that current therapies are associated with pro-arrhythmic risks and anti-arrhythmic agents often have insufficient efficacy partly because effective doses are limited by side-effects.

Ventricular arrhythmia, especially sustained ventricular tachycardia (VT) and ventricular fibrillation (VF) is the main cause of death associated with heart attack. Historically, three types of antiarrhythmic agents, class I agents, β-adrenergic blockers (class II), amiodarone and sotalol, appeared to offer the best scope for mortality reduction in patients with cardiac disease by preventing the occurrence of VT/VF.

The outcome of CAST (Cardiac Arrhythmia Supression Trial, *N. Engl. J. Med.*, 321 (1989) 406-412) and its successor SWORD (Survival With Oral D-sotatol trial, 1994) created much concern regarding the potential of class I agents and sotalol. It was found that class I agents did not decrease mortalities in patient groups at risk from sudden cardiac death. For some subsets of patients, class I agents even proved to increase mortality. The SWORD trial was stopped when sotalol proved to give higher death rate in patients, compared with the placebo. A consequence of these results is that the use of implantable defibrillators and surgical ablation have increased and that the trend in the industry has been towards the development of highly specific class III agents. Some of these channel blockers have been withdrawn from clinical development due to proarrhythmic effects and the subject remains under intensive debate. In this context it should be noted that amiodarone, despite its complex pharmacokinetics, mode of action (amiodarone is not regarded as a pure class III agent) and numerous side effects, is currently considered by many to be the most effective agent in the control of both atrial and ventricular arrhythmia.

Thyrotoxicosis is the clinical syndrome that results when tissues are exposed to elevated levels of circulating thyroid hormones, thyroxine (3,5,3',5'-tetraiodo-L-thyronine, or $T_4$) and triiodothyronine (3,5,3'-triiodo-L-thyronine, or $T_3$). Clinically, this state often manifest itself in weight loss, hypermetabolism, lowering of serum LDL levels, cardiac arrhythmias, heart failure, muscle weakness, bone loss in postmenopausal women, and anxiety. In most instances, thyrotoxicosis is due to hyperthyroidism, a term reserved for disorders characterized by overproduction of thyroid hormones by the thyroid gland. The ideal treatment of hyperthyroidism would be the elimination of its cause. This is however not possible in the more common diseases producing thyroid hypersecretion. At present, treatment of hyperthyroidism is directed to reduce overproduction of thyroid hormones by inhibiting their synthesis or release, or by ablating thyroid tissue with surgery or radioiodine.

Drugs inhibiting thyroid hormone synthesis, release or peripheral conversion of $T_4$ to $T_3$ include antithyroid drugs (thionamides), iodide, iodinated contrast agents, potassium perchlorate and glucocorticoids. The main action of antithyroid drugs such as methimazole (MMI), carbimazole, and propylthiouracil (PTU), is to inhibit the organification of iodide and coupling of iodotyrosines, thus blocking the synthesis of thyroid hormones. As they neither inhibit iodide transport or block the release of stored thyroid hormones, control of hyperthyroidism is not immediate and in most cases requires 2 to 6 weeks. Factors that determine the speed of restoration of euthyroidism include disease activity, initial levels of circulating thyroid hormones, and intrathyroidal hormone stores. Serious side effects are not common with antithyroid drugs. Agranulocytosis is the the most feared problem and have been observed with both MMI or PTU treatment. Elderly patients may be more susceptible to this side effect, but agranulocytosis can occur in any age group, although less frequently. Inorganic iodide given in pharmacological doses (as Lugol's solution or as saturated solution of potassium iodide, SSKI) decreases its own transport into the thyroid, thus inhibiting iodide organification (the Wolff-Chaikoff effect), and rapidly blocks the release of $T_4$ and $T_3$ from the gland. However, after a few days or weeks, its antithyroid action is lost, and thyrotoxicosis recurs or may worsen. Short-term iodide therapy is used to prepare patients for surgery, usually in combination with a thionamide drug. Iodide is also used in the management of severe thyrotoxicosis (thyroid storm), because of its ability to inhibit thyroid hormone release acutely. Perchlorate interferes with accumulation of iodide by the thyroid. Gastric irritation and toxic reactions limit the long-term use of perchlorate in the management of hyperthyroidism. Glucocorticoids in high doses inhibit the peripheral conversion of $T_4$ to $T_3$. In Graves' hyperthyroidism, glucocorticoids appear to decrease $T_4$ secretion by the thyroid, but the efficiency and duration of this effect is unknown. The aim of surgical treatment or radioiodine therapy of hyperthyroidism is to reduce the excessive secretion of thyroid hormones by removal or destruction of thyroid tissue. Subtotal or near-total thyroidectomy is performed in Graves' disease and toxic multinodular goiter. Restoration of euthyroidism before surgery is mandatory. The classical approach combines a course of thionamide treatment to restore and maintain euthyroidism, and the preoperative administration of iodide for approximately 10 days in order to induce involution of the gland. Propranolol and other beta-adrenergic antagonist drugs are useful in controlling tachycardia and other symptoms of sympathetic activation.

A high affinity ThR antagonist would in principle have the ability to restore euthyrodism quicker than any of the above agents, considered that its action is competitive for the ThR receptor. Such an agent could be used either alone or in combination with the above drugs, alternatively before an ablative treatment. It may also serve as a safer substitute for antithyroid drugs, especially in elderly patients at a high risk of agranulocytosis. Furthermore, hyperthyrodism can aggravate pre-existing heart disease and also lead to atrial fibrillation (AF), congestive heart failure, or worsening of angina pectoris. In the elderly patient, often with mild but prolonged elevation of plasma thyroid hormones, symptoms and signs of heart failure and complicating AF may dominate the clinical picture and mask the more classical endocrine manifestations of the disease.

DESCRIPTION OF THE INVENTION

In accordance with the present invention, compounds are provided which are thyroid receptor ligands, and have the general formula I:

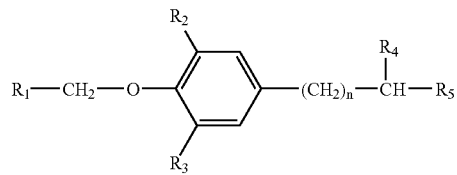

or salts, bioisosteric equivalents, stereoisomers, radioactive derivatives or prodrug ester forms thereof, wherein $R_1$ is selected from: $C_{6-10}$ aryl; $C_{5-10}$ heteroaryl; and $C_{5-10}$ cycloalkyl, said aryl, heteroaryl, cycloalkyl being optionally substituted with 1 to 3 groups $R^a$;

$R_2$ and $R_3$ are the same or different and are selected from: chlorine, bromine, $C_{1-4}$ alkyl, $C_{3-4}$ cycloalkyl, $C_{2-4}$ alkenyl, and $C_{2-4}$ alkynyl, $R_4$ is selected from: halogen, —OH, —SH, —$NH_2$, and —NH($C_{1-4}$);

$R_5$ is selected from: —$CO_2H$, —$PO(OH)_2$, —$PO(OH)NH_2$, —$SO_2OH$, $COCO_2H$, and —$CONHOH$;

$R^a$ is selected from: hydrogen, halogen, $C_{1-4}$ alkyl, $C_{2-4}$ alkenyl, $C_{2-4}$ alkynyl, $C_{1-4}$ alkoxy, $C_{1-4}$ alkylthio, —CN, —$NO_2$, $NH_2$, —NH($C_{1-4}$), and —N($C_{1-4}$)$_2$;

n is 1 or 2.

DETAILED DESCRIPTION OF THE INVENTION

The following definitions apply to the terms as used throughout this specification, unless otherwise limited in specific instances.

The term "thyroid receptor ligand" as used herein is intended to cover any chemical substance which binds to a thyroid receptor. The ligand may act as an antagonist, an agonist, a partial antagonist or a partial agonist.

The term "alkyl" as employed herein alone or as part of another group refers to an acyclic straight or branched chain radical, containing 1 to 4 carbons, such as methyl, ethyl, propyl, butyl in the normal chain radical. Alkyl also refers to a radical where 1 to 3 hydrogens can be replaced by halogen through the available carbons. When $R_2$ and $R_3$ is selected from alkyl and is substituted by halogen, the preferred group radicals are —$CF_3$, —$CHF_2$ and —$CH_2F$.

The term "alkenyl" as used herein by itself or as part of another group refers to straight or branched chain radicals of 2 to 4 carbons and at least one carbon to carbon double bond. Preferably one carbon to carbon double bond is present. Examples of normal chain radicals are ethenyl, propenyl and butenyl. As described above with respect to "alkyl", the straight or branched portion of the alkenyl group may be substituted by halogen.

The term "alkynyl" as used herein by itself or as part of another group refers to straight or branched chain radicals of 2 to 4 carbons and at least one carbon to carbon triple bond. Preferably one carbon to carbon triple bond is present. Examples of normal chain radicals are ethynyl, propynyl and butynyl. As described above with respect to the "alkyl", the straight or branched portion of the alkenyl group may be substituted by halogen. when a substituted alkynyl group is provided.

The term "cycloalkyl" as employed herein alone or as part of another group refers to saturated cyclic hydrocarbon groups or partially unsaturated cyclic hydrocarbon groups, independently containing 1 to 2 carbon to carbon double bonds or carbon to carbon triple bonds. The cyclic hydrocarbon contain 5 to 10 carbons, including rings that are fused. Preferred cycloalkyl groups include 5 to 7 carbons, such as cyclopropyl, cyclobutyl, cyclopentyl, cyclohexyl, cycloheptyl, which may be optionally substituted through available carbons with 1 to 3 groups selected from Ra, which groups may be the same or different. It should also be understood that the present invention also includes compounds with a cycloalkyl ring where 1 to 2 carbons in the ring are replaced by either —O—, —S— or —N—, thus forming a saturated or partially saturated heterocycle. Examples of such rings are piperidine, piperazine, morpholine, thiomorpholine, pyrrolidine, oxazolidine, thiazolidine, tetrahydrofurane, tetrahydrothiophene and the like. Preferred heterocyclic rings are 5- or 6-membered, and may be optionally substituted at available carbons as in the case of "alkyl".

The term "aryl" as employed herein alone or as part of another group refers to monocyclic, bicyclic and tricyclic aromatic groups, consisting of 6 to 10 carbons in the ring portion, including partially saturated rings such as indanyl and tetrahydronaphthyl. The preferred aryl groups are phenyl and naphthyl, which may be substituted with 1 to 3 groups selected from $R^a$ which groups may be the same or different.

The term "halogen" or "halo" as used herein alone or as part of another group, exemplified by "haloalkoxy" or "haloalkyl", refers to fluorine, chlorine, bromine and iodine. When halogen is selected from $R_3$ and $R_4$ the preferred halogen is bromine.

The term "alkoxy" refers to those groups of the designated number of carbon atoms in either a straight or branched configuration attached through an oxygen linkage and, if two or more carbons in length, they may include a double or a triple bond. Examples of such alkoxy groups are methoxy, ethoxy, propoxy, allyloxy, propargyloxy, butoxy, isobutoxy, tertiary butoxy, and the like. Alkoxy also refers to a radical where 1 to 3 hydrogens can be replaced by halogen at available carbons. When $R_2$ is selected from alkoxy and substituted by halogen, the preferred group radicals are —OCF$_3$, —OCHF$_2$ and —OCH$_2$F.

The term "Thio" as used herein as a part of another group, exemplified by "alkylthio", refers to a carbon-sulphur-carbon bond and may also include higher oxidation states of sulphur, such as sulfoxides —SO— and sulphones —SO$_2$—. "Alkylthio" also refers to a radical where 1 to 3 hydrogens can be replaced by halogen through the available carbons. When $R_2$ is selected from alkoxy and substituted by halogen, the preferred group radicals are —SCF$_3$, —SCHF$_2$ and —SCH$_2$F.

The term "heteroaryl" as used herein alone or as a part of another group refers to a group containing 5 to 10 atoms, where the aromatic ring includes 1 to 4 heteroatoms, as nitrogen, oxygen or sulfur. Such rings may be fused to another aryl or heteroaryl ring, and includes possible N-oxides. The heteroaryl group may optionally be substituted at the available carbons with 1 to 3 substituents of $R^a$ which groups may be the same or different.

The term "phosphonic acid" and "phosphamic acid" refers to a phosphorus containing group of the structures:

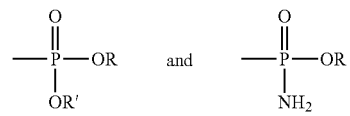

wherein R and R' are independently selected from hydrogen, $C_{1-4}$ alkyl, $C_{2-4}$ alkenyl or $C_{2-4}$ alkynyl.

The term radical "—N(C$_{1-4}$)$_2$" or "—NH(C$_{1-4}$)" refers to a secondary or tertiary amine where "C" is equal to 1, 2, 3, or 4 carbons in a branched or straight chain. Radicals covered by the above definition include: —N(C$_{1-4}$ alkyl)$_2$, —NH(C$_{1-4}$ alkyl), —N(C$_{2-4}$ alkenyl)$_2$, —NH(C$_{2-4}$ alkenyl), —N(C$_{2-4}$ alkynyl)$_2$, —NH(C$_{2-4}$ alkynyl), —N(C$_{1-4}$ alkyl)(C$_{2-4}$ alkenyl), —N(C$_{2-4}$ alkyl)(C$_{2-4}$ alkynyl), and —N(C$_{2-4}$ alkenyl)(C$_{2-4}$ alkynyl).

The term "bioisosteric equivalents" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience: New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev. (Washington, D.C.)* 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thomber C W, "Isosterism and molecular modification in drug design", *Chem. Soc. Rev.* 1979, 8, 563-80.

The compounds of formula I can be present as salts, preferably pharmaceutically acceptable salts. A compound having at least one acid group (for example —COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, in the isolation or purification of free compounds I or their pharmaceutically acceptable salts, are also included. Preferred salts of the compounds of formula I which include an acid group include sodium, potassium and magnesium salts and pharmaceutically acceptable organic amines.

The compounds of formula I having at least one basic center (for example —NH— in piperidine) can also form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. Salts which are unsuitable for pharmaceutical uses but which can be employed, for example, for the isolation or purification of free compounds I or their pharmaceutically acceptable salts, are also included. Preferred salts of the compounds of formula I which include a basic groups include monohydrochloride, hydrogensulfate, methanesulfonate, phosphate or nitrate.

An acid center (for example —COOH) part in formula I can form "prodrug ester forms" known in the art such as pivaloyloxymethyl or dioxolenylmethyl. Such prodrug esters are described in standard references such as Chapter 31, written by Camille G. Wermuth et al., in "The Practice of Medicinal Chemistry", ed. C. G. Wermuth, Academic Press, 1996 (and the references contained therein).

Compounds of the invention are "stereoisomers", which have one or more asymmetric centers and can exist in the form of racemates, single enantiomers, as individual diastereomers, with all possible isomers, and mixtures thereof, all of which are within the scope of the invention.

A preferred embodiment of formula I is when $R_5$ is a carboxylic acid group (—$CO_2H$).

Another preferred embodiment of formula I is when $R_5$ is a carboxylic acid group (—$CO_2H$) and n is 1.

Yet another preferred embodiment of formula I is when $R_5$ is a carboxylic acid group (—$CO_2H$), and $R_3$ and $R_4$ is halogen.

Yet another preferred embodiment of formula I is when n is 1 and $R_3$ and $R_4$ are bromine.

Yet another preferred embodiment of formula I is when $R_5$ is a carboxylic acid group (—$CO_2H$), n is 1, and $R_3$ and $R_4$ is bromine.

In yet another preferred embodiment, compounds of formula I are selected from:

2-Amino-3-[3,5-dibromo-4-(3-bromobenzyloxy)phenyl] propionic acid;

2-Amino-3-[3,5-dibromo-4-(3-trifluormethylbenzyloxy) phenyl]propionic acid;

2-Amino-3-[3,5-dibromo-4-(3,5-dimethylbenzyloxy)phenyl]propionic acid;

3-[3,5-Dibromo-4-(naphthalen-2-ylmethoxy)phenyl]-2-hydroxypropionic acid;

3-[3,5-Dibromo-4-(3-bromobenzyloxy)phenyl]-2-hydroxypropionic acid;

3-[3,5-Dibromo-4-(3-bromobenzyloxy)phenyl]-2-chloropropionic acid;

3-[3,5-Dibromo-4-(pyridin-2-ylmethoxy)phenyl]-2-hydroxypropionic acid;

2-Amino-3-[4-(bistrifluoromethylbenzyloxy)-3,5-dibromophenyl]propionic acid;

2-Amino-3-[3,5-dibromo-4-(pyridin-2-ylmethoxy)phenyl] propionate triethylammonium;

2-Amino-3-[3,5-dibromo-4-(3-trifluoromethoxybenzyloxy) phenyl]propionate triethylammonium;

2-Amino-3-[3,5-dibromo-4-(3-fluoro-5-trifluoromethoxybenzyloxy)phenyl]-propionate triethylammonium;

2-Amino-3-[3,5-dibromo-4-(3-fluorobenzyloxy)phenyl] propionate triethyl-ammonium;

2-Amino-3-[3,5-dibromo-4-(3,5-difluorobenzyloxy)phenyl] propionate triethyl-ammonium;

2-Amino-3-{3,5-dibromo-4-[3-(difluoromethoxy)benzyloxy]phenyl}propionate triethylammonium;

2-Amino-3-[3,5-dibromo-4-(pyridin-4-ylmethoxy)phenyl] propionate triethyl-ammonium;

2-Amino-3-[3,5-dibromo-4-(5-methylisoxazol-3-ylmethoxy)phenyl]propionic acid;

2-Amino-3-[3,5-dibromo-4-(3,5-dichlorobenzyloxy)phenyl]propionate triethyl-ammonium;

2-Amino-3-[3,5-dibromo-4-(2-fluorobenzyloxy)phenyl] propionic acid;

2-Amino-3-[3,5-dibromo-4-(2-methylthiazol-4-ylmethoxy) phenyl]propionate triethylammonium;

2-Amino-3-[3,5-dibromo4-(3-chlorobenzyloxy)phenyl]propionate triethyl-ammonium;

2-Amino-3-[3,5-dibromo-4-(2-chlorobenzyloxy)phenyl] propionate triethyl-ammonium;

2-Amino-3-[3,5-dibromo-4-(3-iodobenzyloxy)phenyl]propionic acid;

and pharmaceutically acceptable salts thereof, and stereoisomers thereof.

The compounds of formula I may be prepared by the processes exemplified in the following reaction schemes. Examples of reagents and procedures for these reactions appear hereinafter and in the working Examples.

Compounds of formula I of the invention where $R_4$ is equal to an amino group, $R_5$ is a carboxylic acid, $R_2$, $R_3$ is bromine and where variation is introduced at the $R_1$ position can be prepared using the method outlined below and indicated in Scheme 1 (Examples 1-3 and 8-22). In the method, phenol 1 is regioselective dibrominated employing elemental bromine in acetic acid in the presence of a buffer such as sodium acetate to give 2. A huge collection of methods for the dibromination of phenols is available in the literature, several which could be applied in the present method and are well known to those skilled in the art.

Phenol 2 is dissolved in a suitable solvent, such as acetone or acetonitrile, treated with 1-5 molar equivalents of a base such as potassium carbonate, cesium carbonate, potassium hydroxide, sodium hydride or triethylamine. The resulting anion is then O-alkylated with the appropriate halides R—Br or R—Cl. Several other combinations of alkylating agents, bases and solvents may be employed and are known to those skilled in the art. For example, alternative alkylating agents can be oxygen-containing such as R—OTs, R—OMs and R—OTf, or nitrogen-containing as diazo compounds. The reaction mixture is heated until the starting materials are consumed yielding 3. After standard work-up, the ester function (—CO$_2$R') is hydrolyzed by treatment with a base and solvent combination, such as sodium hydroxide in methanol (Examples 1-3) or lithium hydroxide in tetrahydrofuran (Examples 8-22). The reaction mixture gives after acidification with hydrochloric acid (Examples 1-3) or neutralization on a SCX SPE column (Examples 8-22) an intermediate, where the protected amine (—NHR, where R is tert-butoxycarbonyl) is hydrolyzed by treatment with trifluoroacetic acid to give the end product 4. In Examples 8-22, the preparations are done in a more automatic fashion. For example, the intermediates and the final products are all purified on short plugs of C18 SPE or silica SPE.

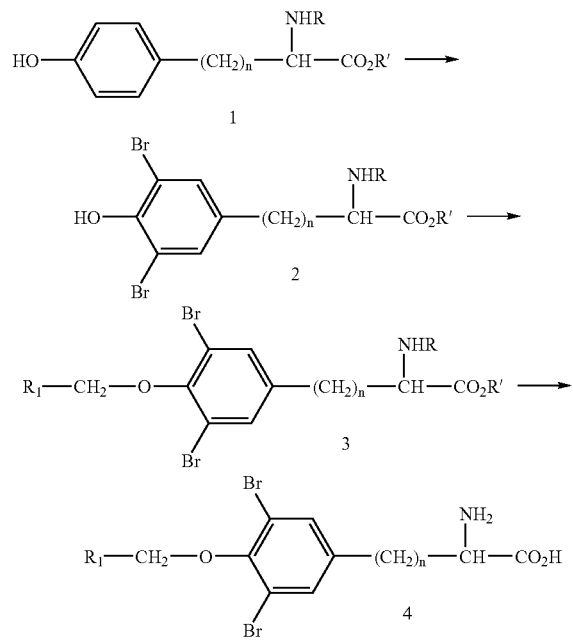

Several other related methodologies exist for the hydrolysis of alkyl esters and tert-butylcarbonylamines and are known to those skilled in the art. Furthermore, other protecting groups for carboxylic acids and amines can be employed, and their usage is known to those skilled in the art (references describing protecting group strategy include, for example, "Protecting Groups in Organic Chemistry", J. F. W. McOmie, Plenum Press, London, New York, 1973, and "Protective Groups in Organic Synthesis", T. W. Greene, Wiley, New York, 1984).

Compounds of formula I of the invention where R$_4$ is equal to a hydroxy group (—OH), R$_5$ is a carboxylic acid, R$_2$, R$_3$ is bromine and where variation is introduced at the R$_1$ position, can be prepared using the method as indicated in Scheme 2 below (Examples 4, 5 and 7). A method similar as above is used, but the reaction sequence is shorter compared with above since the R$_4$ hydroxy group needs no protecting group.

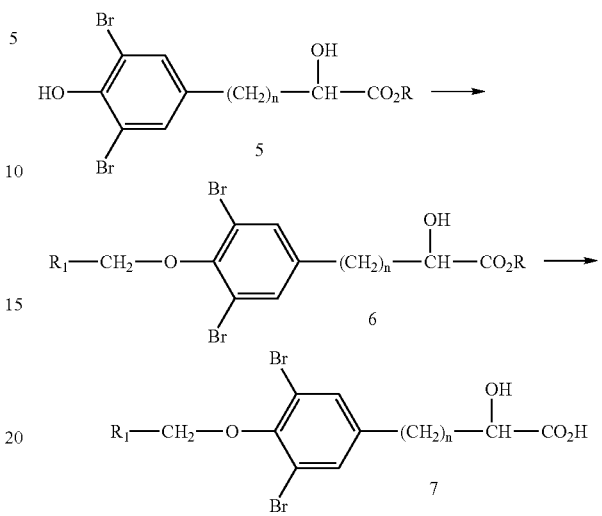

For those skilled in the art it is obvious that a similar method as above can be applied when compounds where R$_4$ is equal to a thio group (—SH) are prepared.

Further compounds of formula I of the invention where R$_4$ is equal to a halogen can be prepared using the method as indicated in Scheme 3 below (Example 6). Amine 8 is diazotated and reacted with an activated olefin, to give the addition product 9. This type of reaction is well known in the literature and is known as the Meerwein arylation reaction (For a review, see Dombrovskii *Russ. Chem. Rev.* 1984, 53, 943-955). Any alternative to this method should be obvious for those skilled in the art. Bromination, coupling and deprotection to give end compound 12 can be done in a similar way as described above.

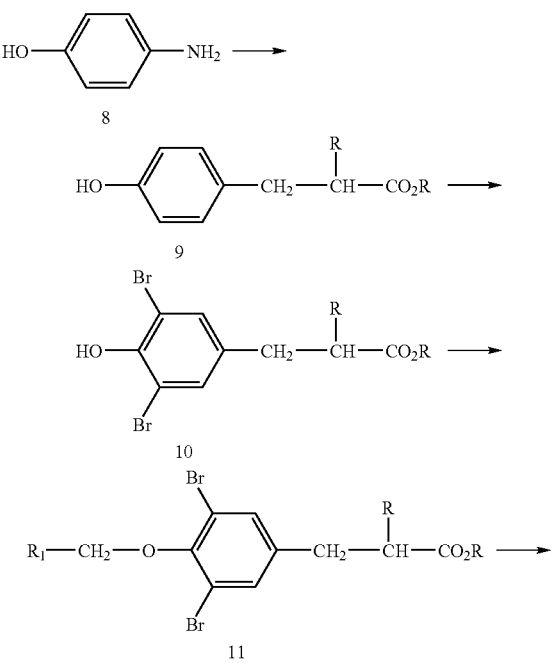

-continued

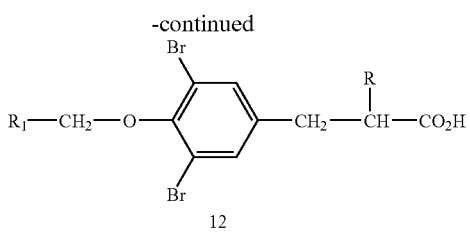

R = Cl

The compounds of the invention are antagonists or partial antagonists, preferably α-selective. As such they are expected to be useful in medical therapy. In particular, they are expected to be useful in the prevention, inhibition or treatment of a disease which is dependent on the expression of a $T_3$ regulated gene or associated with metabolic dysfunction. Examples of such diseases are heart related disorders, such as cardiac arrhythmias (atrial and ventricular arrhythmias), especially atrial fibrillation and ventricular tachycardia and fibrillation. The compounds of the invention may also be useful for the treatment of thyrotoxicosis, especially in the therapy of elderly patients, subclinical hyperthyroidism, and other related endocrine disorders related to thyroid hormone.

Compounds of the invention may also be $T_3$ antagonists with a preferential hepatic activity, and may be useful in medical treatment to improve the clinical course of various liver diseases such as: alcoholic liver disease, viral (Hepatis A,B,C,D,E) liver diseases, and immunological liver diseases. The $T_3$-antagonist may have principal activity in the liver, and thus have a preferential hepatic activity, with minimal activity in the rest of the body to reduce side-effects associated with the treatment. It is known that induction of a state with abnormally low levels of circulating thyroid hormones (hypothyroidism) is a rewarding treatment of liver diseases as hepatic cirrhosis/fibrosis. Nevertheless, induction of hypothyroidism it is not an accepted therapy for liver diseases. The major reason is that currently available methods to induce hypothyroidism inevitably leads to a general hypothyroid state since the thyroid glands production of $T_4$ is blocked. General, systemic hypothyroidism causes a number of unacceptable clinical symptoms such as myxedema, depression, constipation etc. Also, the time of onset from initiation of therapy until hypothyroidism is manifest is rather long, typically months. $T_3$-receptor antagonists do also induce hypothyroidism but much faster than standard therapies. A $T_3$-receptor antagonist with major accumulation in the liver does spare the body from the deleterious impact of general hypothyroidism. The compounds of the invention may therefore be used to treat certain liver diseases, such as chronic alcoholism, acute hepatitis, chronic hepatitis, hepatitis C-induced liver cirrhosis, and liver fibrosis.

The compounds of the invention may also be used to treat certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Another embodiment of the invention is a method of treating, inhibiting or preventing a disease which is dependent on the expression of a $T_3$ regulated gene or associated with metabolic dysfunction in a mammal in need thereof by administering to the mammal a therapeutically effective amount of any of the compounds or pharmaceutical compositions described above. The said diseases may be heart related disorders, such as cardiac arrhythmias (atrial and ventricular arrhythmias), especially atrial fibrillation and ventricular tachycardia and fibrillation, especially in the therapy of elderly patients, subclinical hyperthyroidism, and other related endocrine disorders related to thyroid hormone.

Yet another embodiment of the invention is a method of treating, inhibiting or preventing certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

Further exemplifying the invention is the use of any of the compounds described above in the preparation of a medicament for the treatment, inhibition or prevention of a disease which is dependent on the expression of a $T_3$ regulated gene or is associated with a metabolic dysfunction. Still further exemplifying the invention is the use of any of the compounds described above in the preparation of a medicament for the treatment and/or prevention of heart related disorders, such as cardiac arrhythmias (atrial and ventricular arrhythmias), especially atrial fibrillation and ventricular tachycardia and fibrillation, especially in the therapy of elderly patients, subclinical hyperthyroidism, and other related endocrine disorders related to thyroid hormone.

Further exemplifying the invention is the use of any of the compounds described above in the preparation of a medicament for the treatment, inhibition or prevention of certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

The compounds of the present invention can be administered in such oral dosage forms as tablets, capsules (each of which may include sustained release or timed release formulations), pills, powder, granules, elixirs, tinctures, suspensions, syrups and emulsions. Likewise, they may also be administered intravenous (bolus or infusion), intraperitoneal, topical (e.g., ocular eyedrop), subcutaneous, intramuscular, or transdermal (e.g., patch) form, all using forms well known to those of ordinary skill in the pharmaceutical arts.

The dosage regimen utilizing the compounds of the present invention is selected in accordance with a variety of factors including type, species, age, weight, sex, and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches will known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, exipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms includes sodium oleate, sodium stearate, magnesium stearate, sodium benzoate, sodium acetate, sodium chloride and the like. Disintegrators include without limitation starch, methylcellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed form a variety of phospholipids, such as cholesterol, stearylamine or phosphatidylcholines.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example in "Design of Prodrugs" ed. H. Bundgaard, Elsevier, 1985, which is incorporated by reference herein in its entirety. Metabolites of the compounds includes active species produced upon introduction of compounds of this invention into the biological milieu.

EXAMPLES

The following Examples represent preferred embodiments of the present invention. However, they should not be construed as limiting the invention in any way. The $^1$H NMR spectra were all consistent with the assigned structures in the Examples.

Example 1

2-Amino-3-[3,5-dibromo-4-(3-bromobenzyloxy) phenyl]propionic acid (a) N-(tert-butoxycarbonyl)tyrosine methyl ester (2 g) was dissolved in glacial acetic acid (100 mL). Sodium acetate (1.2 g) and a few drops of water was added under stirring, followed by drop-wise addition bromine (0.8 mL). After 16 hours, the reaction mixture was treated with sodium thiosulphate until the orange colour disappeared. The reaction mixture was concentrated and the residue subjected to column chromathography (silica gel, iso-hexane/ethylacetate). This gave 2.55 g (84%) of methyl-2-tert-butoxycarbonyl-amino-3-(3,5-dibromo-4-hydroxyphenyl) propionate as a white solid mass. LC-MS (electrospray): m/z 454 (M+1).

(b) A mixture of methyl-2-tert-butoxycarbonylamino-3-(3,5-dibromo-4-hydroxy-phenyl) propionate (0.15 g, 0.33 mmol) and potassium carbonate (0.14 g, 1.0 mmol) in acetone (10 mL) was stirred at room temperature. After 10 minutes 3-bromobenzyl bromide (0.25 g, 1.0 mmol) was added. The reaction mixture was heated at reflux for one hour, cooled down to room temperature and concentrated in vacuo. Diethyl ether was added to the residue and the mixture filtered through a celite pad. The resulting filtrate was concentrated and the residue was dissolved in methanol (20 mL). An aqueous solution of sodium hydroxide (1.7 mL, 1 N) was added dropwise and the reaction mixture was stirred over night at room temperature. The solution was acidified with hydrochloric acid (2 N) and the volatiles were removed in vacuo. The residue was collected, washed with water and purified by column chromatography (silica gel, chloroform/methanol 9:1). The intermediate methyl-2-tert-butoxycarbonylamino-3-[3,5-dibromo-4-(3-bromobenzyloxy)phenyl]-propionic acid was dissolved in dichloromethane (10 mL) and trifluoroacetic acid (0.22 mL, 2.87 mmol) was added dropwise. After four hours stirring at room temperature, an aqueous solution of potassium carbonate (saturated) was added until a pH of approximately 7 to 8 was obtained. The reaction mixture was concentrated in vacuo and the residue purified by HPLC (Zorbax CombiHT, SB-C8, 50×21.2 mm 5μ; Mobile phase: solvent A, water with 0.5% formic acid, solvent B, acetonitrile; Gradient: 2 min 80% A, then to 5% of B during 8 min). This gave 20 mg (12%) of 2-amino-3-[3,5-dibromo-4-(3-bromobenzyloxy) phenyl]propionic acid. LC-MS (electrospray): m/z 508, 510 (M+1).

Example 2

2-Amino-3-[3,5-dibromo-4-(3-trifluormethylbenzyloxy)phenyl]propionic acid

To a stirred mixture of methyl-2-tert-butoxycarbonylamino-3-(3,5-dibromo-4-hydroxyphenyl) propionate (0.20 g, 0.44 mmol), potassium carbonate (0.15 g, 1.1 mmol) and acetone (15 mL) was added 3-trifluormethyl benzylbromide (0.26 g, 1.1 mmol). The procedure followed was the same as described in Example 1, but the isolation on column chromatography of the intermediate methyl-2-tert-butoxycarbonylamino-3-[3,5-dibromo-4-(3-trifluormethylbenzyloxy)phenyl]propionic acid was not done. Purification of the final residue by HPLC, using the same conditions as described in Example 1(b), gave 20 mg (9%) of 2-amino-3-[3,5-dibromo-4-(3-trifluormethylbenzyloxy)phenyl]propionic acid. LC-MS (electrospray): m/z 498 (M+1).

Example 3

2-Amino-3-[3,5-dibromo-4-(3,5-dimethylbenzyloxy)phenyl]propionic acid

Methyl-2-tert-butoxycarbonylamino-3-(3,5-dibromo-4-hydroxyphenyl)-propionate (0.20 g, 0.44 mmol) was coupled with 3,5-dimethyl benzylbromide (0.22 g, 1.1 mmol), using the method described in Example 2. After deprotection and final purification on HPLC, using the same conditions as described in Example 1(b), 70 mg (35%) of 2-amino-3-[3,5-dibromo-4-(3,5-dimethylbenzyloxy)phenyl]propionic acid was obtained. LC-MS (electrospray): m/z 458 (M+1).

Example 4

3-[3,5-Dibromo-4-(naphthalen-2-ylmethoxy)phenyl]-2-hydroxypropionic acid (a) Concentrated hydrochloric acid (12 N, 0.7 mL) was added carefully at room temperature under nitrogen to a solution of 2-hydroxy-3-(4-hydroxyphenyl)propionic acid monohydrate (11 mmol) in methanol (25 mL). The light yellow solution was stirred for 20 hours at room temperature under nitrogen. After concentration of the reaction mixture, the light yellow residue was dissolved in ethyl acetate (80 mL) and washed with a saturated aqueous solution of sodium bicarbonate (40 mL). The aqueous layer was extracted with dichloromethane (2×30 mL). The combined organic layers were concentrated in vacuo and filtrated through magnesium sulphate and silica gel. This gave 1.6 g of 2-hydroxy-3-(4-hydroxyphenyl)propionic acid methyl ester as a colourless oil. LC/MS (electrospray): m/z 195 (M−1).

(b) To a mixture of 2-hydroxy-3-(4-hydroxyphenyl)propionic acid methyl ester (8.1 mmol), sodium acetate (24 mmol), acetic acid (85 mL) and some drops of water, bromine (24 mmol) was added carefully at room temperature. The orange solution was stirred for 20 hours at room temperature in the dark. The orange reaction mixture was quenched with an aqueous solution of sodium thiosulphate. The obtained light yellow mixture was concentrated in vacuo, diluted with ethyl acetate (50 mL) and washed with water (2×250 mL). The organic layer was dried over magnesium sulphate and concentrated in vacuo. The residue was purified on column (silica gel, n-heptane/ethyl acetate 3:2). This gave 1.9 g of 3-(3,5-dibromo-4-hydroxyphenyl)-2-hydroxypropionic acid methyl ester as a colourless solid mass. LC/MS (electrospray): m/z 353 (M−1).

(c) A mixture of 3-(3,5-dibromo-4-hydroxyphenyl)-2-hydroxypropionic acid methyl ester (0.25 mmol) and potassium carbonate (0.3 mmol) in acetonitrile (5 mL) was stirred for 10 minutes at room temperature under nitrogen. 2-Bromomethylnaphthalene (0.3 mmol) dissolved in acetonitrile (1 mL) was added with a syringe. The reaction mixture was stirred for 15 hours at room temperature under nitrogen. After concentration in vacuo, the light yellow residue was diluted with ethyl acetate (20 mL) and washed with brine (25 mL). The organic phase was dried over magnesium sulphate and concentrated in vacuo. The residue was purified on column (ethyl acetate/n-heptane 1:3). The fractions containing the coupled material were pooled, concentrated and dissolved in methanol (10 mL), and an aqueous solution of lithium hydroxide (10 mL, 1N) was added carefully. The reaction mixture was stirred for 15 hours at room temperature, acidified with hydrochloric acid (2 N) and the volatile solvents removed in vacuo. The formed precipitate was collected, washed with water and purified with HPLC (YMC-Pack, D-C8-5, 250×20 mm, 5 μm, 120A; Mobile phase: 40% acetonitrile and 60% 25 mM ammonium acetate). This gave 11 mg (9%) of 3-[3,5-dibromo-4-(naphthalen-2-ylmethoxy)phenyl]-2-hydroxypropionic acid as a white solid mass. LC/MS (electrospray): m/z 479 (M−1).

Example 5

3-[3,5-Dibromo-4-(3-bromobenzyloxy)phenyl]-2-hydroxypropionic acid 3-(3,5-Dibromo-4-hydroxyphenyl)-2-hydroxypropionic acid methyl ester (0.25 mmol) was coupled with 1-bromo-3-bromomethylbenzene and hydrolyzed using the method described in Example 4(c). This gave 51 mg (40%) of 3-[3,5-dibromo-4-(3-bromo-benzyloxy)phenyl]-2-hydroxypropionic acid as a white solid mass. LC/MS (electrospray): m/z 507 (M−1).

Example 6

3-[3,5-Dibromo-4-(3-bromobenzyloxy)phenyl]-2-chloropropionic acid

Sodiumnitrite (0.12 mol) dissolved in water (25 mL) was added slowly at −40° C. to a suspension of 4-aminophenol (0.11 mol) and concentrated hydrochloric acid (12 N, 25 mL) in acetone (125 mL). The temperature of the reaction was not allowed to exceed −10° C. during the addition. The dark mixture was stirred for 45 minutes below 10° C. and methyl acrylate (0.56 mol) was added. The suspension was then heated to 30° C. and copper(I) iodide (0.0025 mol) was added carefully such that the temperature did not exceed 32° C. The still dark suspension was stirred at 30° C. for 30 minutes and at room temperature for 3 days. After concentration of the reaction mixture, the dark residue was taken up in dichloromethan (200 mL) and washed with water (250 mL). The aqueous layer was extracted with dichloromethan (2×200 mL). The combined organic layers were washed with water (3×250 mL) and brine (250 mL), dried over magnesium sulphate and concentrated under reduced pressure. The dark red residue was purified with HPLC (YMC-Pack, D-C8-5, 250×20 mm, 5 μm, 120A; Mobile phase: 30% acetonitrile and 70% 25 mM ammonium acetate). This gave 4.7 g of 2-chloro-3-(4-hydroxyphenyl)propionic acid methyl ester as a pale yellow solid. GC/MS (EI): m/z 214.6 (M$^+$).

(b) 2-chloro-3-(4-hydroxyphenyl)propionic acid methyl ester (0.47 mmol) was brominated using the method described in Example 4(b). This gave 160 mg of 3-(3,5-dibromo-4-hydroxyphenyl)-2-chloropropionic acid methyl ester as a white solid mass. LC/MS (electrospray): m/z 371.6 (M−1).

(c) 3-(3,5-dibromo-4-hydroxyphenyl)-2-chloropropionic acid methyl ester (0.35 mmol) was coupled with 1-bromo-3-bromomethylbenxene and hydrolysed using the method described in Example 4(c). This gave 20 mg of 3-[3,5-dibromo-4-(3-bromo-benzyloxy)phenyl]-2-chloropropionic acid. LS/MS (electrospray): m/z 526 (M−1).

Example 7

3-[3,5-Dibromo-4-(pyridin-2-ylmethoxy)phenyl]-2-hydroxypropionic acid 3-(3,5-dibromo-4-hydroxyphenyl)-2-hydroxypropionic acid methyl ester (0.25 mmol) was coupled with 2-chloromethylpyridine and hydrolyzed using a modified method of the method as described in Example 4(c). A catalytic amount of sodium iodide was added the the reaction mixture during the coupling step. This gave 16 mg (15%) of 3-[3,5-dibromo-4-(pyridin-2-ylmethoxy)phenyl]-2-hydroxypropionic acid as a white solid mass. LC/MS (electrospray): m/z 430 (M−1).

General Procedure for the Preparation of Examples 8-22

To a solution of methyl-2-tert-butoxycarbonylamino-3-(3,5-dibromo-4-hydroxy-phenyl)propionate (0.035 mmol) in dry acetonitrile (0.25 mL) was added potassium carbonate (0.11 mmol), and the resulting mixture was stirred at room temperature. After 10 minutes a solution of the appropriate halide (0.070 mmol) in acetonitrile or acetonitrile/acetone 1:1 (0.25 mL) was added. When the halide was a chloride, a catalytic amount of sodium iodide was added to the reaction mixture (Examples 9, 15, 16, 17, 18 and 19). The reaction mixture was heated at 80° C. over night. After cooling down to room temperature, the reaction mixture was filtered through a silica SPE column (500 mg/3 mL), eluting with n-heptane/ethyl acetate 1:1 (3 mL). After concentration in vacuo the residue was dissolved in tetrahydrofuran (0.25 mL) and lithium hydroxide (1 N in water, 0.25 mL) was added.

The reaction mixture was stirred at room temperature. After 4 hours the mixture was neutralised on an SCX SPE column (500 mg/3 mL) using methanol (Examples 8, 16, 18 and 22) or triethylamine (10% in methanol) (Examples 9, 10, 11, 12, 13, 14, 15, 17, 19, 20 and 21) as eluent. The filtrate was concentrated and the residue purified on a silica SPE column (500 mg/3 mL) with n-heptane/ethyl acetate 9:1 (3 mL) followed by dichloromethane/methanol 9:1 (3 mL). The product containing fractions were collected and concentrated in vacuo. The residue was deprotected using trifluoroacetic acid (10% in dichloromethane, 0.5 mL) for four hours at room temperature. After concentration, the mixture was dissolved in a minimum amount of dimethyl sulfoxide containing trifluoroacetic acid (10%), and purified on an SPE C18 column (500 mg/3 mL) using water (2 mL) followed by acetonitrile/water 1:1 (3 mL) as eluents. The product containing fractions were collected and concentrated in vacuo.

Example 8

2-Amino-3-[4-(bistrifluoromethylbenzyloxy)-3,5-dibromophenyl]propionic acid

Methyl-2-tert-butoxycarbonylamino-3-(3,5-dibromo-4-hydroxyphenyl)propionate (0.035 mmol) was coupled with 2-bromomethyl-3,5-bistrifluoromethylbenzene and hydrolyzed using the method described in "General procedure for the preparation of Examples 8-22". This gave 16% yield of 2-amino-3-[-(bistrifluoromethylbenzyloxy)-3,5-dibromophenyl]propionic acid. LC/MS (electrospray): m/z 564 (M−1).

Example 9

2-Amino-3-[3,5-dibromo-4-(pyridin-2-ylmethoxy)phenyl]propionate triethylammonium Methyl-2-tert-butoxycarbonylamino-3-(3,5-dibromo-4-hydroxyphenyl)propionate (0.035 mmol) was coupled with 2-chloromethylpyridine and hydrolyzed using the method described in "General procedure for the preparation of Examples 8-22". This gave 21% yield of 2-amino-3-[3,5-dibromo-4-(pyridin-2-ylmethoxy)phenyl]propionate triethylammonium. LC/MS (electrospray): m/z 429 (M−1).

Example 10

2-Amino-3-[3,5-dibromo-4-(3-trifluoromethoxybenzyloxy)phenyl]propionate triethylammonium Methyl-2-tert-butoxycarbonylamino-3-(3,5-dibromo-4-hydroxyphenyl)propionate (0.035 mmol) was coupled with 1-bromomethyl-3-trifluoromethoxybenzene and hydrolyzed using the method described in "General procedure for the preparation of Examples 8-22". This gave 12% yield of 2-amino-3-[3,5-dibromo-4-(3-trifluoromethoxybenzyloxy)-phenyl]propionate triethylammonium. LC/MS (electrospray): m/z 512 (M−1).

Example 11

2-Amino-3-[3,5-dibromo-4-(3-fluoro-5-trifluoromethoxybenzyloxy)phenyl]propionate triethylammonium Methyl-2-tert-butoxycarbonylamino-3-(3,5-dibromo-4-hydroxyphenyl)propionate (0.035 mmol) was coupled with 1-bromomethyl-3-fluoro-5-trifluoromethylbenzene and hydrolyzed using the method described in "General procedure for the preparation of Examples 8-22". This gave 6% yield of 2-amino-3-[3,5-dibromo-4-(3-fluoro-5-trifluoromethoxybenzyloxy)phenyl]propionate triethylammonium. LC/MS (electrospray): m/z 514 (M−1).

Example 12

2-Amino-3-[3,5-dibromo-4-(3-fluorobenzyloxy)phenyl]propionate triethylammonium

Methyl-2-tert-butoxycarbonylamino-3-(3,5-dibromo-4-hydroxyphenyl)propionate (0.035 mmol) was coupled with 1-bromomethyl-3-fluorobenzene and hydrolyzed using the method described in "General procedure for the preparation of Examples 8-22". This gave 10% yield of 2-Amino-3-[3, 5-dibromo-4-(3-fluorobenzyloxy)phenyl]propionate triethylammonium. LC/MS (electrospray): m/z 446 (M−1).

Example 13

2-Amino-3-[3,5-dibromo-4-(3,5-difluorobenzyloxy) phenyl]propionate triethylammonium Methyl-2-tert-butoxycarbonylamino-3-(3,5-dibromo-4-hydroxyphenyl)propionate (0.035 mmol) was coupled with 1-bromomethyl-3,5-difluorobenzene and hydrolyzed using the method described in "General procedure for the preparation of Examples 8-22". This gave 13% yield of 2-amino-3-[3,5-dibromo-4-(3-fluorobenzyloxy)phenyl]propionate triethylammonium. LC/MS (electrospray): m/z 464 (M−1).

Example 14

2-Amino-3-{3,5-dibromo-4-[3-(difluoromethoxy) benzoloxy]phenyl}propionate triethylammonium Methyl-2-tert-butoxycarbonylamino-3-(3,5-dibromo-4-hydroxyphenyl)propionate (0.035 mmol) was coupled with 1-bromomethyl-3-(1,1-difluoromethoxy)benzene and hydrolyzed using the method described in "General procedure for the preparation of Examples 8-22". This gave 15% yield of 2-amino-3-{3,5-dibromo-4-[3-(difluoromethoxy) benzyloxy]phenyl}propionate triethylammonium. LC/MS (electrospray): m/z 494 (M−1).

Example 15

2-Amino-3-[3,5-dibromo-4-(pyridin-4-ylmethoxy) phenyl]propionate triethylammonium Methyl-2-tert-butoxycarbonylamino-3-(3,5-dibromo-4-hydroxyphenyl)propionate (0.035 mmol) was coupled with 4-chloromethylpyridine and hydrolyzed using the method described in "General procedure for the preparation of Examples 8-22". This gave 13% yield of 2-amino-3-[3,5-dibromo-4-(pyridin-4-ylmethoxy)phenyl]propionate triethylammonium. LC/MS (electrospray): m/z 429 (M−1).

Example 16

2-Amino-3-[3,5-dibromo-4-(5-methylisoxazol-3-ylmethoxy)phenyl]propionic acid

Methyl-2-tert-butoxycarbonylamino-3-(3,5-dibromo-4-hydroxyphenyl)propionate (0.035 mmol) was coupled with 3-chloromethyl-5-methylisoxazole and hydrolyzed using the method described in "General procedure for the preparation of Examples 8-22". This gave 22% yield of 2-amino-3-[3,5-dibromo-4-(5-methylisoxazol-3-ylmethoxy)phenyl] propionic acid. LC/MS (electrospray): m/z 433 (M−1).

Example 17

2-Amino-3-[3,5-dibromo-4-(3,5-dichlorobenzyloxy) phenyl]propionate triethylammonium Methyl-2-tert-butoxycarbonylamino-3-(3,5-dibromo-4-hydroxyphenyl)propionate (0.035 mmol) was coupled with 1-bromomethyl-3,5-dichlorobenzene and hydrolyzed using the method described in "General procedure for the preparation of Examples 8-22". This gave 5% yield of 2-amino-3-[3,5-dibromo-4-(5-methylisoxazol-3-ylmethoxy)phenyl] propionic acid. LC/MS (electrospray): m/z 496 (M−1).

Example 18

2-Amino-3-[3,5-dibromo-4-(2-fluorobenzyloxy) phenyl]propionic acid

Methyl-2-tert-butoxycarbonylamino-3-(3,5-dibromo-4-hydroxyphenyl)propionate (0.035 mmol) was coupled with 1-bromomethyl-2-fluorobenzene and hydrolyzed using the method described in "General procedure for the preparation of Examples 8-22". This gave 10% yield of 2-amino-3-[3,5-dibromo-4-(2-fluorobenzyloxy)phenyl]propionic acid. LC/MS (electrospray): m/z 446 (M−1).

Example 19

2-Amino-3-[3,5-dibromo-4-(2-methylthiazol-4-ylmethoxy)phenyl]propionate triethylammonium Methyl-2-tert-butoxycarbonylamino-3-(3,5-dibromo-4-hydroxyphenyl)propionate (0.035 mmol) was coupled with 4-chloromethyl-2-methylthiazole and hydrolyzed using the method described in "General procedure for the preparation of Examples 8-22". This gave 12% yield of 2-amino-3-[3,5-dibromo-4-(5-methylisoxazol-3-ylmethoxy)phenyl]propionic acid. LC/MS (electrospray): m/z 449 (M−1).

Example 20

2-Amino-3-[3,5-dibromo-4-(3-chlorobenzyloxy) phenyl]propionate triethylammonium

Methyl-2-tert-butoxycarbonylamino-3-(3,5-dibromo-4-hydroxyphenyl)propionate (0.035 mmol) was coupled with 1-bromomethyl-3-chlorobenzene and hydrolyzed using the method described in "General procedure for the preparation of Examples 8-22". This gave 5% yield of 2-amino-3-[3,5-dibromo-4-(3-chlorobenzyloxy)phenyl]propionate triethylammonium. LC/MS (electrospray): m/z 462 (M−1).

Example 21

2-Amino-3-[3,5-dibromo-4-(2-chlorobenzyloxy) phenyl]propionate triethylammonium

Methyl-2-tert-butoxycarbonylamino-3-(3,5-dibromo-4-hydroxyphenyl)propionate (0.035 mmol) was coupled with 1-bromomethyl-2-chlorobenzene and hydrolyzed using the method described in "General procedure for the preparation of Examples 8-22". This gave 23% yield of 2-amino-3-[3,5-dibromo-4-(2-chlorobenzyloxy)phenyl]propionate triethylammonium. LC/MS (electrospray): m/z 462 (M−1).

Example 22

2-Amino-3-[3,5-dibromo-4-(3-iodobenzyloxy)phenyl]propionic acid

Methyl-2-tert-butoxycarbonylamino-3-(3,5-dibromo-4-hydroxyphenyl)propionate (0.035 mmol) was coupled with 1-bromomethyl-3-iodobenzene and hydrolyzed using the method described in "General procedure for the preparation of Examples 8-22". This gave 38% yield of 2-amino-3-[3,5-dibromo-4-(3-iodobenzyloxy)phenyl]propionic acid. LC/MS (electrospray): m/z 554 (M−1).

The compounds of the invention exhibit binding affinities to the ThRa receptor in the range of 10 nM to 10000 nM.

The invention claimed is:

1. A compound according to formula I:

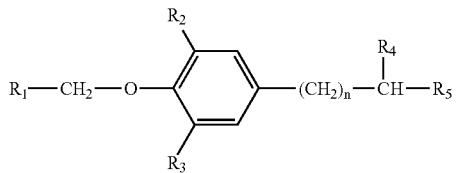

or a salt, stereoisomers, or prodrug ester forms thereof, wherein:

$R_1$ is selected from: $C_{6-10}$ aryl; $C_{5-10}$ heteroaryl; and $C_{5-10}$ cycloalkyl, said aryl, heteroaryl, and cycloalkyl being optionally substituted with 1 to 3 groups $R^a$;

$R_2$ and $R_3$ are the same or different and are selected from: chlorine, bromine, $C_{1-4}$ alkyl, $C_{3-4}$ cycloalkyl, $C_{2-4}$ alkenyl, and $C_{2-4}$ alkynyl;

$R_4$ is selected from: halogen, —OH, —SH, —$NH_2$, and —$NH(C_{1-4})$;

$R_5$ is selected from: —$CO_2H$, —$PO(OH)_2$, —PO(OH)$NH_2$, —$SO_2OH$, $COCO_2H$, and —CONHOH;

$R^a$ is selected from: hydrogen, halogen, $C_{1-4}$ alkyl, $C_{2-4}$ alkenyl, $C_{2-4}$ alkynyl, $C_{1-4}$ alkoxy, $C_{1-4}$ alkylthio, —CN, —$NO_2$, $NH_2$, —$NH(C_{1-4})$, and —$N(C_{1-4})_2$;

n is 1 or 2; all the possible steroisomers thereof, and prodrug ester forms thereof.

2. A compound according to claim 1 wherein $R_5$ is —$CO_2H$.

3. A compound according to claim 2 wherein n is 1.

4. A compound according to claim 2 wherein $R_3$ and $R_4$ are bromine.

5. A compound according to claim 1 wherein $R_3$ and $R_4$ are bromine, and n is 1.

6. A compound according to claim 4 wherein n is 1.

7. A compounds according to claim 1 which is:

2-Amino-3-[3,5-dibromo-4-(3-bromobenzyloxy)phenyl] propionic acid;
2-Amino-3-[3,5-dibromo-4-(3-trifluormethylbenzyloxy) phenyl]propionic acid;
2-Amino-3-[3,5-dibromo-4-(3,5-dimethylbenzyloxy)phenyl]propionic acid;
3-[3,5-Dibromo-4-(naphthalen-2-ylmethoxy)phenyl]-2-hydroxypropionic acid;
3-[3,5-Dibromo-4-(3-bromobenzyloxy)phenyl]-2-hydroxypropionic acid;
3-[3,5-Dibromo-4-(3-bromobenzyloxy)phenyl]-2-chloropropionic acid;
3-[3,5-Dibromo-4-(pyridin-2-ylmethoxy)phenyl]-2-hydroxypropionic acid;
2-Amino-3-[4-(bistrifluoromethylbenzyloxy)-3,5-dibromophenyl]propionic acid;
2-Amino-3-[3,5-dibromo-4-(pyridin-2-ylmethoxy)phenyl]propionate triethylammonium;
2-Amino-3-[3,5-dibromo-4-(3-trifluoromethoxybenzyloxy)phenyl]propionate triethylammonium;
2-Amino-3-[3,5-dibromo-4-(3-fluoro-5-trifluoromethoxybenzyloxy)phenyl]propionate triethylammonium;
2-Amino-3-[3,5-dibromo-4-(3-fluorobenzyloxy)phenyl] propionate triethylammonium;
2-Amino-3-[3,5-dibromo-4-(3,5-difluorobenzyloxy)phenyl]propionate triethylammonium;
2-Amino-3-[3,5-dibromo-4-[3-(difluoromethoxy)benzyloxy]phenyl]propionate triethylammonium;
2-Amino-3-[3,5-dibromo-4-(pyridin-4-ylmethoxy)phenyl]propionate triethylammonium;
2-Amino-3-[3,5-dibromo-4-(5-methylisoxazol-3-ylmethoxy)phenyl]propionic acid;
2-Amino-3-[3,5-dibromo-4-(3,5-dichlorobenzyloxy)phenyl]propionate triethyl ammonium;
2-Amino-3-[3,5-dibromo-4-(2-fluorobenzyloxy)phenyl] propionic acid;
2-Amino-3-[3,5-dibromo-4-(2-methylthiazol-4-ylmethoxy)phenyl]propionate triethylammonium;
2-Amino-3-[3,5-dibromo-4-(3-chlorobenzyloxy)phenyl] propionate triethylammonium;
2-Amino-3-[3,5-dibromo-4-(2-chlorobenzyloxy)phenyl] propionate triethylammonium;
2-Amino-3-[3,5-dibromo-4-(3-iodobenzyloxy)phenyl] propionic acid;

and pharmaceutically acceptable salts, bioisosters, and stereoisomers thereof.

8. A compound according to claim 1, which has one or more asymmetric centers and can exist in the form of a racemate, single or multiple enantiomer, or as a diastereomer.

9. A pharmaceutical composition comprising an effective amount of a compound according to claim 1 together with a pharmaceutically acceptable carrier.

10. The compound of Formula I, wherein said prodrug ester form is pivaloyloxymethyl.

11. The compound of Formula I, wherein said prodrug ester form is dioxolenylmethyl.

* * * * *